US010678332B2

(12) United States Patent
Bodin et al.

(10) Patent No.: US 10,678,332 B2
(45) Date of Patent: Jun. 9, 2020

(54) REMOTELY GUIDING THE POSITIONING OF A MOBILE DEVICE

(71) Applicant: International Business Machines Corporation, Armonk, NY (US)

(72) Inventors: William K. Bodin, Austin, TX (US); Indiver N. Dwivedi, Pune (IN); David Jaramillo, Lake Worth, FL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 173 days.

(21) Appl. No.: 15/422,801

(22) Filed: Feb. 2, 2017

(65) Prior Publication Data

US 2018/0218125 A1  Aug. 2, 2018

(51) Int. Cl.
| | | |
|---|---|---|
| *H04N 7/18* | (2006.01) | |
| *G06F 3/01* | (2006.01) | |
| *H04N 7/14* | (2006.01) | |
| *G16H 40/67* | (2018.01) | |
| *G16H 20/30* | (2018.01) | |

(52) U.S. Cl.
CPC .............. *G06F 3/016* (2013.01); *G16H 20/30* (2018.01); *G16H 40/67* (2018.01); *H04N 7/147* (2013.01)

(58) Field of Classification Search
CPC .. G06F 19/3418; G06F 3/016; G06F 19/3481; H04N 7/14
See application file for complete search history.

(56) References Cited

U.S. PATENT DOCUMENTS

| | | | |
|---|---|---|---|
| 7,830,962 B1 | 11/2010 | Fernandez et al. | |
| 8,405,490 B2 | 3/2013 | Kagermeier et al. | |
| 8,692,774 B2 | 4/2014 | Venon | |
| 9,829,981 B1* | 11/2017 | Ji | G06F 3/016 |
| 2012/0050324 A1* | 3/2012 | Jeong | G06F 17/30 345/633 |
| 2012/0283746 A1 | 11/2012 | Hu et al. | |
| 2013/0121468 A1 | 5/2013 | Ohta et al. | |
| 2013/0207791 A1* | 8/2013 | Olsson | G01V 3/12 340/407.1 |
| 2013/0229272 A1* | 9/2013 | Elliott | G05G 9/047 340/407.2 |
| 2013/0338447 A1* | 12/2013 | Gilad-Gilor | A61B 5/0077 600/300 |
| 2013/0339039 A1 | 12/2013 | Roman et al. | |
| 2014/0176455 A1* | 6/2014 | Araki | G06F 3/016 345/173 |
| 2018/0001192 A1* | 1/2018 | Vaughn | A63F 13/285 |

OTHER PUBLICATIONS

Disclosed Anonymously. (2011). Smarter Real-Time Patient Healthcare. IPCOM000209576D, 8 pages.
Ruffaldi, et al. "Encountered Haptic Augmented Reality Interface for Remote Examination," 2015 IEEE Symposium on 3D User Interfaces, pp. 179-180. doi: 10.1109/3DUI.2015.7131759.

* cited by examiner

*Primary Examiner* — Jonathan R Messmore
(74) *Attorney, Agent, or Firm* — Cantor Colburn LLP; Samuel Waldbaum

(57) ABSTRACT

Embodiments are directed to a computer implemented method that includes receiving, by a recipient device, an instruction to move the recipient device from a current position to a target position. The instruction is received from a director device. The method also includes generating a haptic response based on the received instruction. The haptic response is generated based upon the relative positioning between the current position and the target position.

14 Claims, 4 Drawing Sheets

REMOTELY GUIDING THE POSITIONING OF A MOBILE DEVICE

BACKGROUND

The present invention relates in general to remotely guiding a positioning of a mobile device. More specifically, the present invention relates to the use of haptic feedback communication to remotely guide the positioning of the mobile device.

Advances in imaging and communication technologies have enabled medical professionals (such as doctors, for example) to perform medical examinations and medical procedures on patients that are not physically in the same locations as the medical professionals. The patients can transmit text, voice data, images, and/or video to the doctor, and the doctor can perform medical treatment based on the received text, voice data, images, and/or video.

SUMMARY

According to one or more embodiments of the present invention, a method includes receiving, by a recipient device, an instruction to move the recipient device from a current position to a target position. The instruction is received from a director device. The method also includes generating a haptic response based on the received instruction. The haptic response is generated based upon the relative positioning between the current position and the target position.

According to one or more embodiments of the present invention, a computer system is provided. The computer system includes a processor system communicatively coupled to a memory. The processor system is configured to perform a method including receiving an instruction to move the computer system from a current position to a target position. The instruction is received from a director device. The method also includes generating a haptic response based on the received instruction. The haptic response is generated based upon the relative positioning between the current position and the target position.

According to one or more embodiments of the present invention, a computer program product is provided. The computer program product includes a computer-readable storage medium that has program instructions embodied therewith. The computer-readable storage medium is not a transitory signal per se, and the program instructions are readable by a processor system to cause the processor system to perform a method. The method includes receiving, by a recipient device, an instruction to move the recipient device from a current position to a target position, and the instruction is received from a director device. The method also includes generating a haptic response based on the received instruction. The haptic response is generated based upon the relative positioning between the current position and the target position.

BRIEF DESCRIPTION OF THE DRAWINGS

The subject matter of the present invention is particularly pointed out and distinctly defined in the claims at the conclusion of the specification. The foregoing and other features and advantages are apparent from the following detailed description taken in conjunction with the accompanying drawings in which:

DETAILED DESCRIPTION

Figure 1:
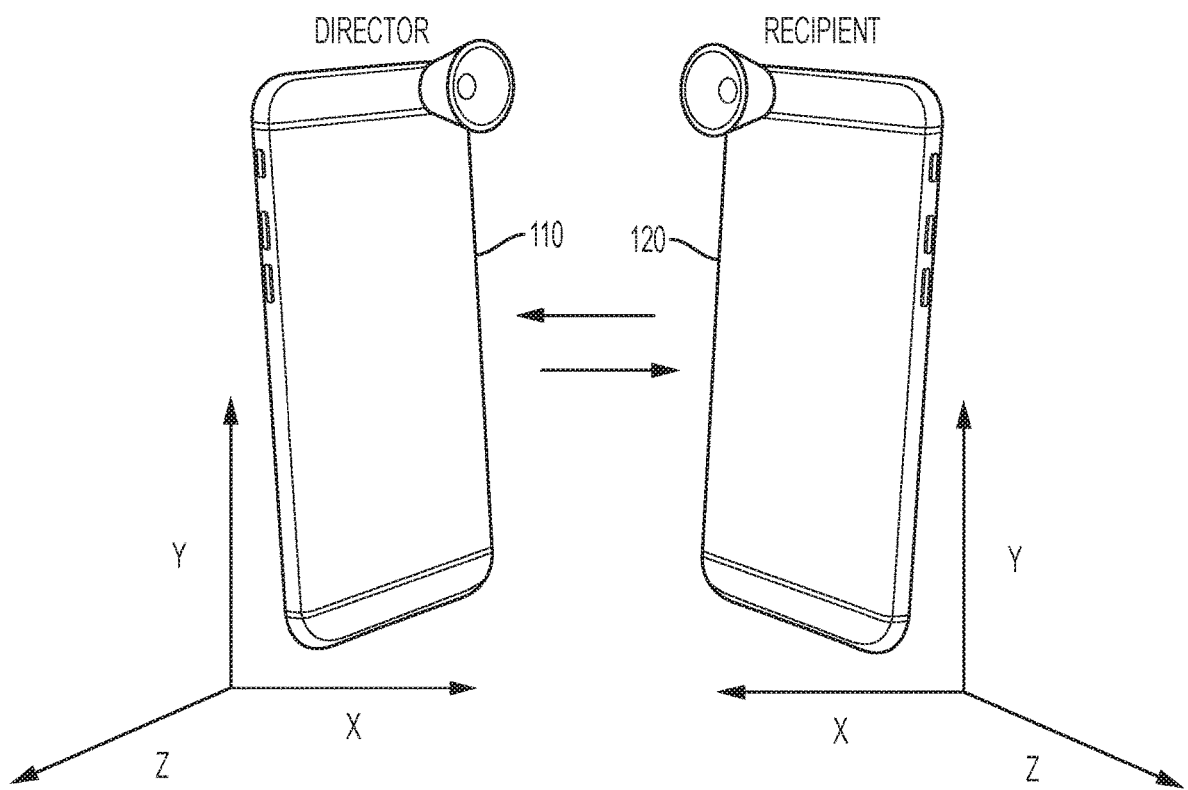
FIG. 1 depicts a method of communicating between a director device and a recipient device in accordance with embodiments of the present invention.

In accordance with one or more embodiments of the invention, methods and computer program products for remotely guiding a positioning of a mobile device are provided. Various embodiments of the present invention are described herein with reference to the related drawings. Alternative embodiments can be devised without departing from the scope of this invention. References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Additionally, although this disclosure includes a detailed description of a computing device configuration, implementation of the teachings recited herein are not limited to a particular type or configuration of computing device(s). Rather, embodiments of the present disclosure are capable of being implemented in conjunction with any other type or configuration of wireless or non-wireless computing devices and/or computing environments, now known or later developed.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

For the sake of brevity, conventional techniques related to computer processing systems and computing models may or may not be described in detail herein. Moreover, it is understood that the various tasks and process steps described herein can be incorporated into a more comprehensive procedure, process or system having additional steps or functionality not described in detail herein.

As new mobile devices emerge in the market, an increasing number of mobile application programs are becoming available. Some of these applications enable medical professionals to remotely monitor the condition of their patients. For example, a doctor can remotely monitor the condition of the doctor's patients using the doctor's mobile device. The doctor can use a mobile phone, tablet, or laptop to talk to the doctor's patient, and the doctor can see the patient on a screen of the mobile device. The doctor can remotely interact with the patient by using software programs that enable video conferencing (programs such as Skype™, for example). When using these video conferencing programs, even if the doctor and the patient are in different locations, the patient can position an imaging device (such as a web camera, for example) in order to capture the necessary images/video of the patient. The images and/or video can then be transmitted to the doctor's mobile device. For example, the doctor can view imagery of the patient on the doctor's mobile phone. The doctor can then also communicate with the patient via the doctor's mobile phone.

However, the current conferencing applications (such as Skype™) do not enable the doctor to remotely control the imaging device (that is positioned at the patient's location). With the current approaches, the doctor generally has to verbally instruct the patient to reposition the imaging device. However, the patient can have difficulty complying with the verbal instructions of the doctor, as verbal instructions can be imprecise.

In view of the above-described difficulties with the current approaches, embodiments of the present invention allow a user (such as, for example, a medical professional) to remotely control and guide an image-capturing device, where the image-capturing device is located at a remote location. As a non-limiting example implementation, embodiments of the invention provide a process of performing a 2-way communication between first and second paired mobile device applications. The first mobile device application is used by a doctor in a first location, and the second mobile device application is used by a patient in a second location remote from the first location. In some embodiments, the patient is assisted by another person (e.g., a medical professional, or the patient's relative) in the second location, and in this case the second mobile device application is used by the person assisting the patient. The doctor holds the first mobile device in space as if the first mobile device were over a body part of the patient. The patient or the person assisting the patient holds another mobile device over the real body part of the patient, for example the patient's ear canal. The doctor moves the first mobile device in space to "virtually" position the first mobile device to view the portion of the patient that the doctor wants to view. The second mobile device provides haptic feedback so that the patient or the person assisting the patient positions the second mobile device to track the position of the first mobile device. When the second remote device has properly tracked the position of the first mobile device, haptic feedback stops, thereby helping the patient or the person assisting the patient to understand that the second mobile device is in the location that the doctor wants to view. As such, a medical professional can use embodiments of the present invention to remotely and accurately guide the image-capturing device to a specific part of a patient's body.

Although the descriptions provided herein explain and describe embodiments of the invention in the context of how the embodiments can be used by medical professionals, the embodiments can also be used by and configured for other types of users. For example, one or more embodiments can be used by an insurance approver (who is assisted on-site by an insurance agent) to perform a remote inspection of a vehicle. As another example, one or more embodiments can also be used by an experienced automobile engineer (who is assisted on-site by a car mechanic) to perform remote inspection of a running car engine. A wide variety of possible users can use one or more embodiments to remotely guide a positioning of a mobile device.

Turning now to a more detailed description of aspects of the invention, FIG. 1 depicts a method of communicating between a director device and a recipient device in accordance with embodiments of the present invention. With embodiments of the present invention, the mobile device (of the medical professional) and the imaging-device (that is located at the patient's location) can form a paired set of devices. Embodiments of the present invention are directed to an automated process of performing a communication between these paired devices. The doctor's mobile device can perform the function of directing the movement of the imaging device, and thus the doctor's mobile device can be generally referred to as a director device 110. The imaging device can be configured to receive guidance from the doctor's mobile device, and thus the imaging device can be generally referred to as a recipient device 120. The director device 110 can remotely control movement and positioning of the recipient device 120 by guiding a remote user (located at the patient's location) to move and position the recipient device 120. The remote user can be the patient, or an assistant to the patient, or a family member of the patient, for example.

With one or more embodiments of the present invention, the doctor can remotely request/control movement of the recipient device by moving the director device. Specifically, embodiments of the present invention can determine the director device's position in three-dimensional space, at the doctor's location. Embodiments of the present invention can also determine the recipient device's position in three-dimensional space, at the patient's location. Embodiments of the present invention then synchronize the position of the doctor's director device and the position of the patient's recipient device.

After the position of the doctor's director device and the position of the patient's recipient device are synchronized, any movement of the doctor's director device will be communicated to the recipient device. The recipient device can be instructed to move in accordance with the director's device. For example, if the director device moves three inches to the right, embodiments of the present invention can inform the recipient device that the recipient device should also move three inches to the right. Similarly, if the director device moves to the left, moves up, moves down, moves closer, or moves away, the recipient device will be instructed to move left, move up, move down, move closer, or move away, respectively.

As described above, the doctor can view imagery of the patient on the doctor's mobile device. For example, the doctor can view the imagery on a visual interface of the doctor's mobile device. In view of the above, with embodiments of the present invention, if the doctor wants to reposition the recipient device to capture different imagery of the patient, the doctor can reposition the recipient device by performing a repositioning of the director device. As mentioned above, the repositioning of the director device will be detected, measured, and communicated to the recipient device. Thus, the remote user is made aware that repositioning is to occur. Therefore, the doctor can remotely position the recipient device in order to obtain the view that is desired by the doctor.

Embodiments of the present invention can also allow a director device to remotely control positioning of the recipient device by allowing the doctor to manually input instructions. For example, embodiments of the present invention can allow the doctor to position the recipient device by allowing the doctor to manually input instructions via a visual interface of the director device. Specifically, with embodiments of the present invention, the doctor can point or click on portions of the visual interface of the director device. This pointing or clicking can indicate, to the recipient device, a specific location that the recipient device should center or focus on. Therefore, the doctor can remotely position the recipient device by inputting manual instructions as well.

As described above, instructions to position the recipient device are communicated to a remote user of the recipient device. Embodiments of the present invention can perform this communication using haptic communication. Specifically, the recipient device can include a system of providing haptic feedback, where the system provides haptic feedback in accordance with the requested movement. As such, because the haptic feedback is configured in accordance with the requested movement, the remote user is informed of the requested movements via the haptic feedback, and the haptic feedback can guide the remote user to properly position the recipient device.

Embodiments of the present invention can configure the intensity of the haptic response in order to be varied based on whether the recipient device is properly moving in accordance with the requested movement. For example, embodiments of the present invention can increase the intensity of a haptic response if the recipient device is moving in a direction that is contrary to the requested movement. For example, if the doctor requests that the recipient device be moved to the right (which causes a corresponding haptic response to guide the remote user to move the recipient device to the right), and if the recipient device is instead moved to the left, then the intensity of the haptic response can increase in order notify the remote user that the recipient device is moving in an incorrect direction. On the other hand, as the recipient device is moved closer to the location that is requested by the director device, the haptic response intensity can decrease. Once the recipient device reaches the target location that is designated by the director device, the haptic response can stop entirely. In view of the above, the remote user (that is positioning the recipient device) can precisely position the recipient device at the target location.

With embodiments of the present invention, the director device and the recipient device can communicate through a software application that is installed on both of the devices. The application that is installed on both of the devices can possibly enable each device to interchangeably perform the functions of recipient device and director device. For example, the application of embodiments of the present invention can enable a phone that is used as a director in one instance to be used as a recipient device in another instance, and vice versa. Further, because the director device can correspond to the doctor's mobile phone, for example, embodiments of the present invention can allow a doctor to remotely position the recipient device in a precise manner by using the doctor's own mobile device, without needing any additional specialized instruments and/or specialized devices.

As described above, movement of the director device and the recipient device can be detected and measured by embodiments of the present invention. The director device and the recipient device can each include accelerometers, and these accelerometers can perform the function of detecting and measuring the movement of the devices. The measured movement of the director device (and/or the target location requested by the director device) can be transmitted to the recipient device, and the remote user of the recipient device can feel a corresponding haptic response. After the remote user feels the haptic response and moves the recipient device, the movement of the recipient device can also be measured. The measured movement of the recipient device can then be compared to the movement of the director device and/or the target location that is requested by the director device. The recipient device can report its location to the director device. If the measured movement of the recipient device does not correspond to the requests of the director device, further haptic responses can be generated by the recipient device to further guide the remote user. Therefore, the haptic responses can guide the movements of the recipient device to conform to the movements requested by the director device. If the measured movement of the recipient device does not correspond to the requests of the director device, either the recipient device and/or the director device can make such determination.

The director device can communicate requested movement to the recipient device by using a gateway server that performs cellular communication, by using Wi-Fi communication, and/or by using any other means of transmitting data. One example protocol for transferring data can be, but is not limited to, user datagram protocol (UDP).

Figure 2:
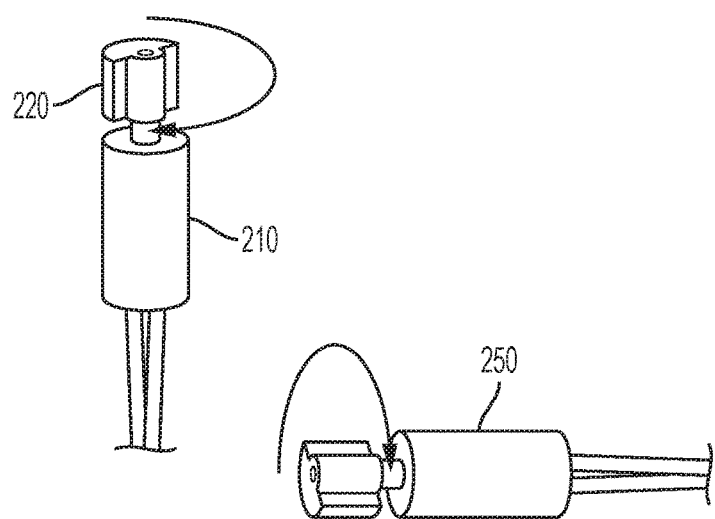
FIG. 2 depicts haptic devices that can be included in a recipient device or a director device in accordance with embodiments of the present invention.

FIG. 2 depicts haptic devices that can be included in a recipient device or a director device, in accordance with embodiments of the present invention. As described above, a system of haptic feedback can be included, at least, within recipient device 120 of FIG. 1. In one example, a haptic feedback engine 210 can rotate an unbalanced weight 220 along an axis to create a torque in a particular direction. Unbalanced weight 220 can be rotated to generate a tactile sensation (of vibration, for example), and the sensation acts as the haptic feedback that is perceived by the remote user. With unbalanced weight 220, the shaft of haptic feedback engine 210 can be considered to be an off-center gravity shaft. Haptic feedback engines can rotate their shafts around different axes. For example, the shaft of haptic feedback engine 210 can be oriented to rotate around a different axis as compared to the shaft of haptic feedback engine 250. A recipient device can include more than one haptic feedback engine, where each feedback engine can be oriented around different corresponding axes. Further, each differently-oriented feedback engine can possibly generate a different tactile sensation.

One or more haptic feedback engines can generate different combinations of tactile sensations, in order to guide the remote user in positioning the recipient device. Each possible direction for positioning the recipient device (in three-dimensional space) can be represented by a specific tactile sensation that is generated by the one or more haptic feedback engines. Therefore, when the remote user detects a specific tactile sensation, the remote user will know that guidance (for positioning the recipient device in a specific direction) is being provided. In one non-limiting example, guidance in the x-direction can be represented by a tactile sensation corresponding to a single long buzzing, while guidance in the y-direction can be represented by a different tactile sensation corresponding to two short buzzes. Alternatively, in another non-limiting example, each possible direction for positioning the recipient device can be indicated by a different haptic feedback engine. For example, guidance in the x-direction can be represented by a tactile sensation generated by a first haptic feedback engine, guidance in the y-direction can be represented by a tactile sensation generated by a second haptic feedback engine, and guidance in the z-direction can be represented by a tactile sensation generated by a combination of both the first and the second haptic feedback engines. Alternatively, instead of providing guidance along different axes, embodiments of the invention can provide guidance along different directions using different tactile sensations. For example, guidance in the left direction can be represented by a first tactile sensation, guidance in the right direction can be represented by a second tactile sensation, guidance in an upward direction can be represented by a third tactile sensation, guidance in a downward direction can be represented by a fourth tactile sensation, etc. Different embodiments can use different combinations of tactile sensations in order to guide the recipient device in different directions.

With embodiments of the present invention, after the remote user senses a specific tactile sensation, the remote user can ascertain that the recipient device is to be moved in a particular direction or axis. Further, as described above, as the remote user moves the recipient device, the remote user can also ascertain whether the recipient device is moving farther or closer to the target location, along the direction or axis. For example, the remote user can ascertain whether the recipient device is moving farther or closer to the target location, based on the intensity of the specific tactile sensation. As described above, if the recipient device is moving farther away from the target location, then the intensity of the tactile sensation can intensify. If the recipient device is moving toward the target location, the intensity of the tactile sensation can be reduced. As the recipient device is being moved, the image/video captured by the recipient device can be delivered to the director device in real time.

Figure 3:
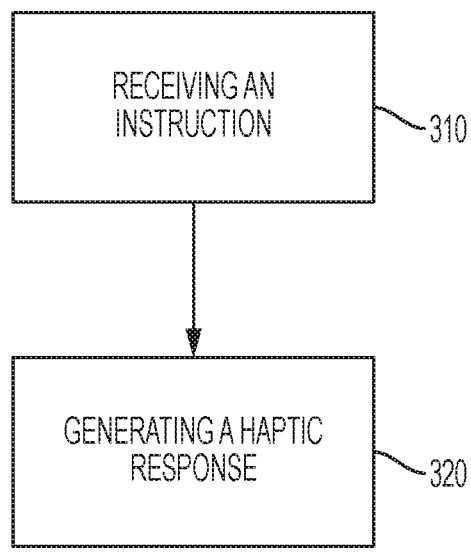
FIG. 3 depicts a flow diagram of a method in accordance with embodiments of the present invention.

FIG. 3 depicts a flow diagram of a method, in accordance with embodiments of the present invention. The method shown in FIG. 3 can be performed by recipient device 120 of FIG. 1, for example. The method can include, at 310, receiving an instruction to move a recipient device from a current position to a target position. The instruction is received from a director device. The method can also include, at 320, generating a haptic response based on the received instruction. The haptic response is generated based upon the relative positioning between the current position and the target position.

Figure 4:
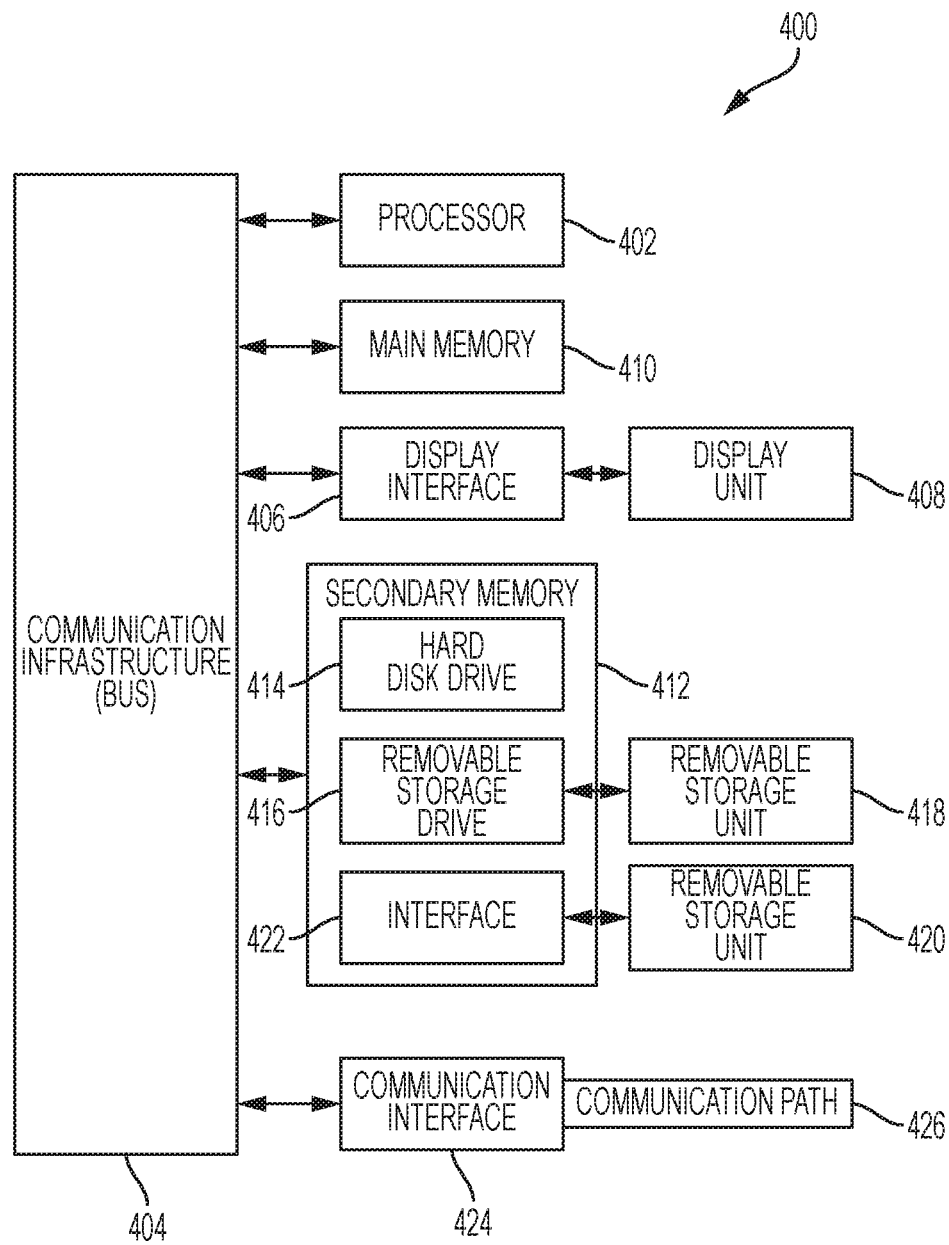
FIG. 4 depicts a high-level block diagram of a computer system, which can be used to implement one or more embodiments.

FIG. 4 depicts a high-level block diagram of a computer system 400, which can be used to implement one or more embodiments. More specifically, computer system 400 can be used to implement hardware components of systems capable of performing methods described herein. Although one exemplary computer system 400 is shown, computer system 400 includes a communication path 426, which connects computer system 400 to additional systems (not depicted) and can include one or more wide area networks (WANs) and/or local area networks (LANs) such as the Internet, intranet(s), and/or wireless communication network(s). Computer system 400 and additional system are in communication via communication path 426, e.g., to communicate data between them.

Computer system 400 includes one or more processors, such as processor 402. Computer system 400 can be implemented within director device 110 and/or within recipient device 120, for example. Processor 402 is connected to a communication infrastructure 404 (e.g., a communications bus, cross-over bar, or network). Computer system 400 can include a display interface 406 that forwards graphics, textual content, and other data from communication infrastructure 404 (or from a frame buffer not shown) for display on a display unit 408. Computer system 400 also includes a main memory 410, preferably random access memory (RAM), and can also include a secondary memory 412. Secondary memory 412 can include, for example, a hard disk drive 414 and/or a removable storage drive 416, representing, for example, a floppy disk drive, a magnetic tape drive, or an optical disc drive. Hard disk drive 414 can be in the form of a solid state drive (SSD), a traditional magnetic disk drive, or a hybrid of the two. There also can be more than one hard disk drive 414 contained within secondary memory 412. Removable storage drive 416 reads from and/or writes to a removable storage unit 418 in a manner well known to those having ordinary skill in the art. Removable storage unit 418 represents, for example, a floppy disk, a compact disc, a magnetic tape, or an optical disc, etc. which is read by and written to by removable storage drive 416. As will be appreciated, removable storage unit 418 includes a computer-readable medium having stored therein computer software and/or data.

In alternative embodiments, secondary memory 412 can include other similar means for allowing computer programs or other instructions to be loaded into the computer system. Such means can include, for example, a removable storage unit 420 and an interface 422. Examples of such means can include a program package and package interface (such as that found in video game devices), a removable memory chip (such as an EPROM, secure digital card (SD card), compact flash card (CF card), universal serial bus (USB) memory, or PROM) and associated socket, and other removable storage units 420 and interfaces 422 which allow software and data to be transferred from the removable storage unit 420 to computer system 400.

Computer system 400 can also include a communications interface 424. Communications interface 424 allows software and data to be transferred between the computer system and external devices. Examples of communications interface 424 can include a modem, a network interface (such as an Ethernet card), a communications port, or a PC card slot and card, a universal serial bus port (USB), and the like. Software and data transferred via communications interface 424 are in the form of signals that can be, for example, electronic, electromagnetic, optical, or other signals capable of being received by communications interface 424. These signals are provided to communications interface 424 via communication path (i.e., channel) 426. Communication path 426 carries signals and can be implemented using wire or cable, fiber optics, a phone line, a cellular phone link, an RF link, and/or other communications channels.

In the present description, the terms "computer program medium," "computer usable medium," and "computer-readable medium" are used to refer to media such as main memory 410 and secondary memory 412, removable storage drive 416, and a hard disk installed in hard disk drive 414. Computer programs (also called computer control logic) are stored in main memory 410 and/or secondary memory 412. Computer programs also can be received via communications interface 424. Such computer programs, when run, enable the computer system to perform the features discussed herein. In particular, the computer programs, when run, enable processor 402 to perform the features of the computer system. Accordingly, such computer programs represent controllers of the computer system. Thus it can be seen from the forgoing detailed description that one or more embodiments provide technical benefits and advantages.

Figure 5:
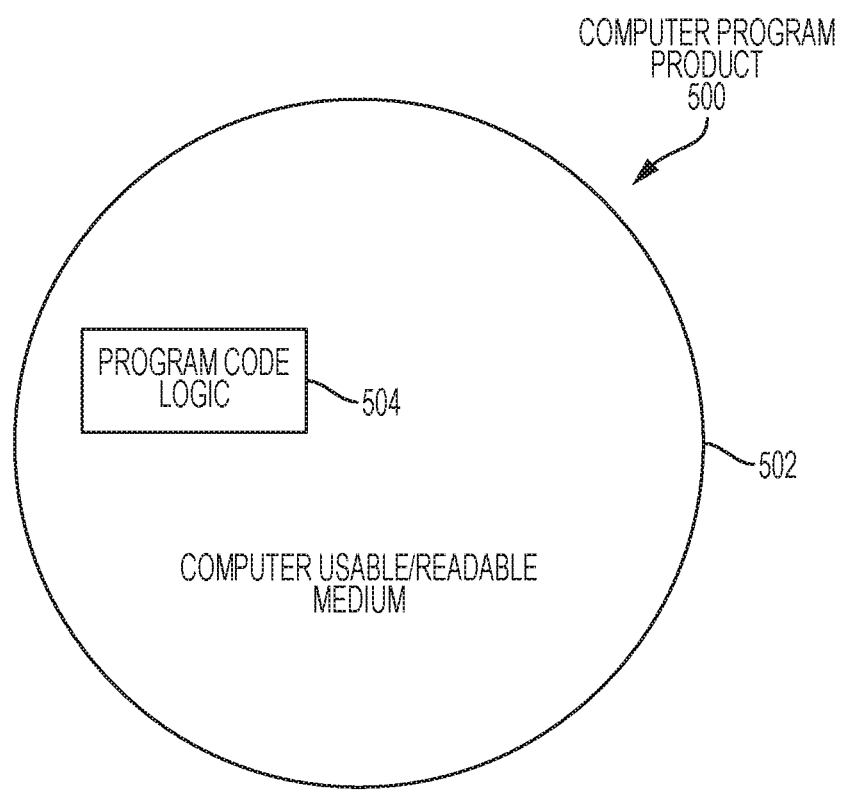
FIG. 5 depicts a computer program product in accordance with an embodiment of the present invention.

Referring now to FIG. 5, a computer program product 500 in accordance with an embodiment that includes a computer-readable storage medium 502 and program instructions 504 is generally shown.

Embodiments can be a system, a method, and/or a computer program product. The computer program product can include a computer-readable storage medium (or media) having computer-readable program instructions thereon for causing a processor to carry out aspects of embodiments of the present invention.

The computer-readable storage medium can be a tangible device that can retain and store instructions for use by an instruction execution device. The computer-readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out embodiments can include assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer-readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer-readable program instructions by utilizing state information of the computer-readable program instructions to personalize the electronic circuitry, in order to perform embodiments of the present invention.

Aspects of various embodiments are described herein with reference to flowchart illustrations and/or block diagrams of methods, apparatus (systems), and computer program products according to various embodiments. It will be understood that each block of the flowchart illustrations and/or block diagrams, and combinations of blocks in the flowchart illustrations and/or block diagrams, can be implemented by computer-readable program instructions.

These computer-readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions can also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments described herein.

What is claimed is:

1. A computer implemented method comprising:
   transmitting, by a recipient device, a captured imagery of a current position to a director device;
   receiving, by the recipient device, an instruction to move the recipient device from the current position to a target position, wherein the instruction is received from the director device, and wherein the recipient device and the director device are configured to interchangeably perform functions of the recipient device and the director device;
   generating a haptic response based on the received instruction, wherein the haptic response is generated based upon the relative positioning between the current position and the target position, wherein the haptic response comprises two or more different tactile sensations, each of the two or more different tactile sensations indicating a particular direction or axis upon which the recipient device to be moved in a three dimensional space, in order for the recipient device to be moved to the target position, and wherein the instruction for each axis upon which the recipient device to be moved in the three dimensional space is provided by a different haptic feedback engine; and
   transmitting a captured imagery of the target position to the director device.

2. The computer implemented method of claim 1 further comprising synchronizing the current position of the recipient device with a position of the director device, wherein the instruction comprises an instruction to move the recipient device in accordance with a movement of the director device.

3. The computer implemented method of claim 1, wherein the intensity of the haptic response is based on the distance between the current position and the target position, and the intensity of the haptic response intensifies as the distance increases.

4. The computer implemented method of claim 1 further comprising ending the generation of the haptic response when the recipient device is moved to the target position.

5. The computer implemented method of claim 1, wherein the haptic response is generated via at least one small torque engine, and the at least one small torque engine comprises an off-center gravity shaft.

6. A computer system comprising:
   a memory; and
   a processor system communicatively coupled to the memory;
   the processor system configured to perform a method comprising:
      transmitting a captured imagery of a current position to a director device;
      receiving an instruction to move the computer system from the current position to a target position, wherein the instruction is received from the director device and wherein a recipient device and the director device are configured to interchangeably perform functions of the recipient device and the director device;
      generating a haptic response based on the received instruction, wherein the haptic response is generated based upon the relative positioning between the current position and the target position, wherein the haptic response comprises two or more different tactile sensations, each of the two or more different tactile sensations indicating a particular direction or axis upon which the recipient device to be moved in a three dimensional space, in order for the recipient device to be moved to the target position, and wherein the instruction for each axis upon which the recipient device to be moved in the three dimensional space is provided by a different haptic feedback engine; and
      transmitting a captured imagery of the target position to the director device.

7. The computer system of claim 6, wherein the method further comprises synchronizing the current position of the computer system with a position of the director device, wherein the instruction comprises an instruction to move the computer system in accordance with a movement of the director device.

8. The computer system of claim 6, wherein the intensity of the haptic response is based on the distance between the current position and the target position, and the intensity of the haptic response intensifies as the distance increases.

9. The computer system of claim 6, wherein the method further comprises ending the generation of the haptic response when the computer system is moved to the target position.

10. The computer system of claim 6, wherein:
    the haptic response is generated via at least one small torque engine; and
    the at least one small torque engine comprises an off-center gravity shaft.

11. A computer program product comprising:
    a non-transitory computer-readable storage medium having program instructions embodied therewith, wherein the computer-readable storage medium is not a transitory signal per se, the program instructions readable by a processor system to cause the processor system to perform a method comprising:
    transmitting a captured imagery of a current position to a director device;
    receiving, by the recipient device, an instruction to move the recipient device from the current position to a target position, wherein the instruction is received from the director device, and wherein a recipient device and the director device are configured to interchangeably perform functions of the recipient device and the director device;
    generating a haptic response based on the received instruction, wherein the haptic response is generated based upon the relative positioning between the current position and the target position, wherein the haptic response comprises two or more different tactile sensations, each of the two or more different tactile sensations indicating a particular direction or axis upon which the recipient device to be moved in a three dimensional space, in order for the recipient device to be moved to the target position, and wherein the instruction for each axis upon which the recipient device to be moved in the three dimensional space is provided by a different haptic feedback engine; and transmitting a captured imagery of the target position to the director device.

12. The computer program product of claim 11, wherein the method performed by the processor system further comprises synchronizing the current position of the recipient device with a position of the director device, wherein the instruction comprises an instruction to move the recipient device in accordance with a movement of the director device.

13. The computer program product of claim 11, wherein the intensity of the haptic response is based on the distance between the current position and the target position, and the intensity of the haptic response intensifies as the distance increases.

14. The computer program product of claim 11, wherein the method performed by the processor system further comprises ending the generation of the haptic response when the recipient device is moved to the target position.

* * * * *